(12) United States Patent
Masyada

(10) Patent No.: US 6,946,106 B1
(45) Date of Patent: Sep. 20, 2005

(54) PAPER CURRENCY STERILIZATION SYSTEM

(76) Inventor: Francis Masyada, 11415 126 Ave. North, Largo, FL (US) 33778

(*) Notice: Subject to any disclaimer, the term of this patent is extended or adjusted under 35 U.S.C. 154(b) by 564 days.

(21) Appl. No.: 10/083,190

(22) Filed: Feb. 26, 2002

(51) Int. Cl.[7] ................................................. A61L 2/04
(52) U.S. Cl. .................... 422/307; 162/359.1; 162/375
(58) Field of Search ..................... 422/307; 162/286, 162/290, 358.1, 359.1, 361, 375

(56) References Cited

U.S. PATENT DOCUMENTS 5,626,822 A * 5/1997 Kadowaki et al. .......... 422/307
6,701,637 B2 * 3/2004 Lindsay et al. ................ 34/71

* cited by examiner

*Primary Examiner*—Elizabeth McKane
(74) *Attorney, Agent, or Firm*—Edward P. Dutkiewicz

(57) ABSTRACT

A paper sterilization system comprises a chamber having one wall with an input slot and another wall with an output slot. A conveyor system is comprised of two co-acting belts, and upper and a lower. The belts are in facing contact. A plurality of rollers is provided. The rollers are adapted to convey the belts in contact with each other and with paper through the chamber from the input slot to the output slot. Also provided is a heating element. The heating element is adapted to increase the temperature to between about 150 and 400 degrees Fahrenheit. A pressure assembly is provided. The pressure assembly is adapted to increase the pressure to between about 1 and 4 atmospheres. Drive members are provided. The drive members are adapted to drive the belt and paper at a speed sufficient to kill viral and fungal organisms on paper moving through the chamber.

5 Claims, 5 Drawing Sheets

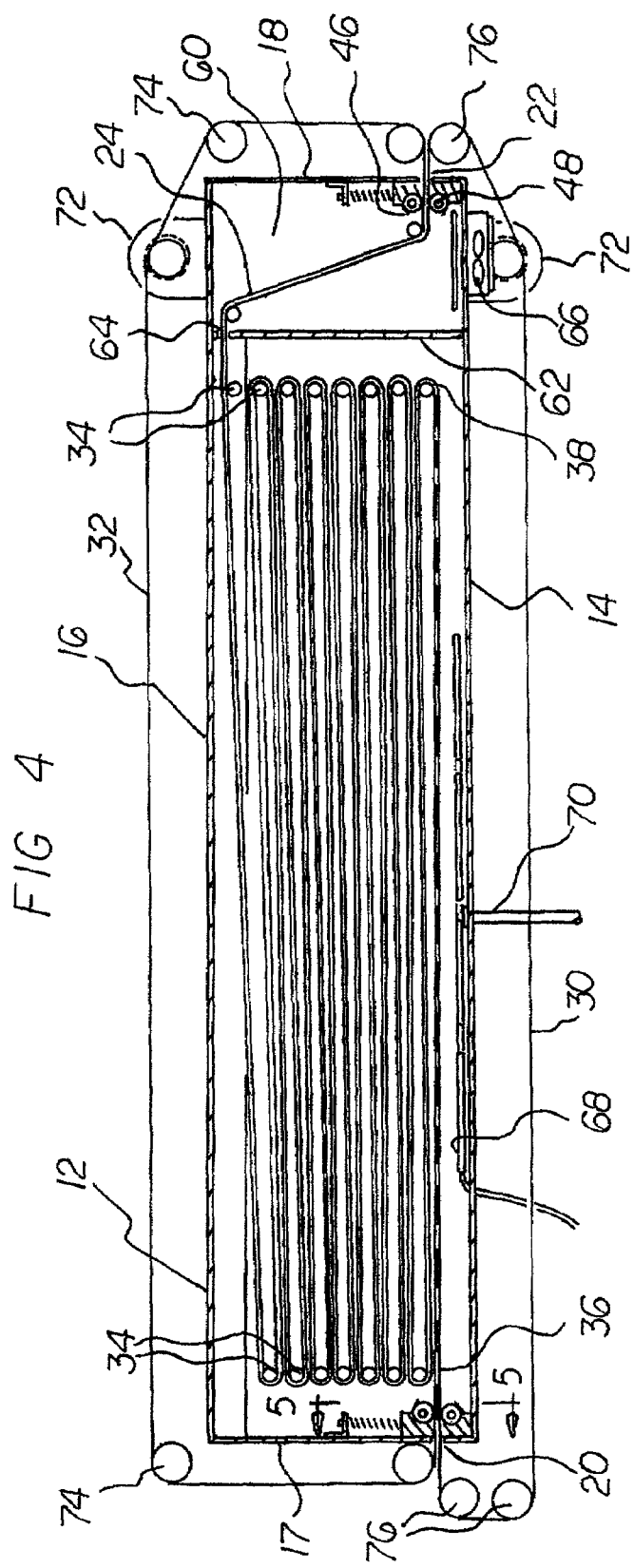

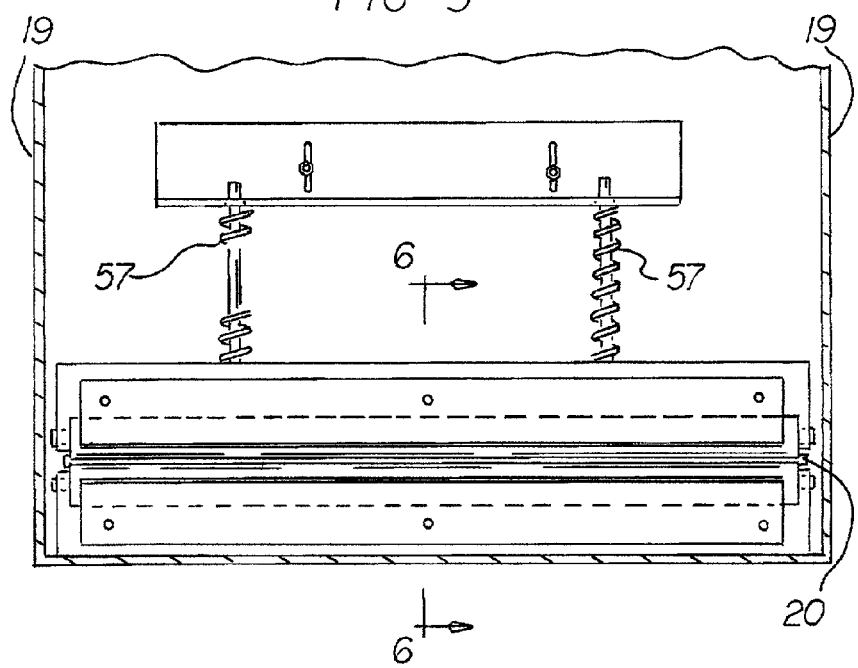
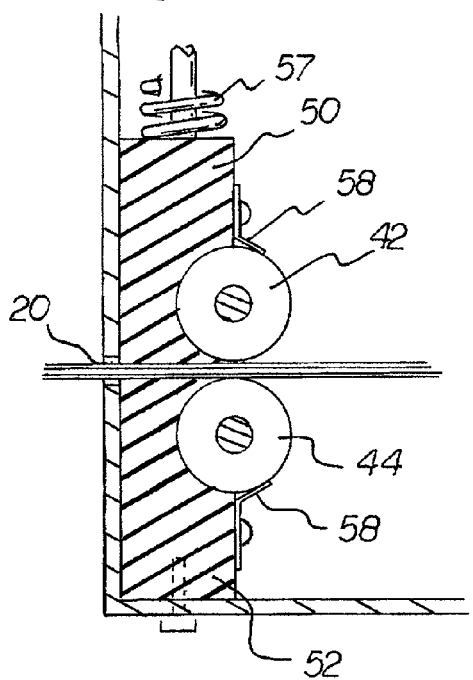

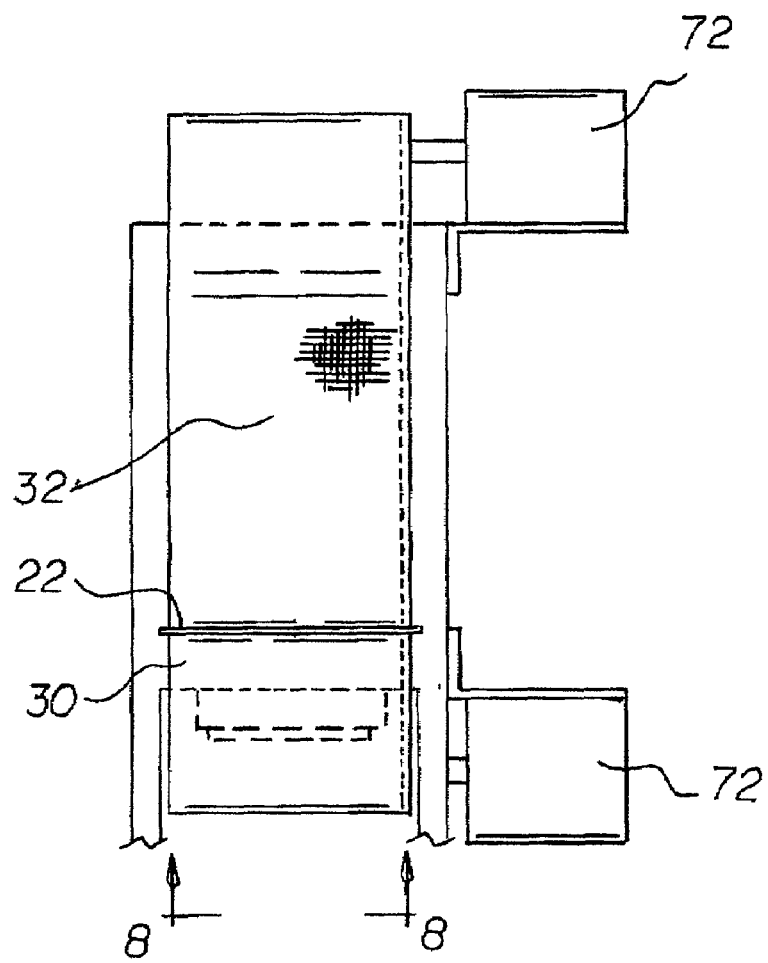
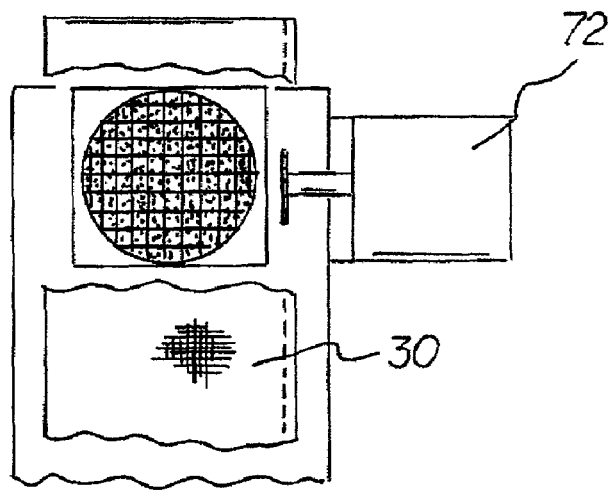

PAPER CURRENCY STERILIZATION SYSTEM

BACKGROUND OF THE INVENTION

1. Field of the Invention

The present invention relates to a paper currency sterilization system and more particularly pertains to killing all viral and fungal microorganisms on paper currencies.

2. Description of the Prior Art

The use of paper cleaning devices of known designs and configurations is known in the prior art. More specifically, paper cleaning devices of known designs and configurations previously devised and utilized for the purpose of killing various types of viral and fungal microorganisms by conventional methods and apparatuses are known to consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, the aforementioned patents do not describe a paper currency sterilization system that allows killing all viral and fungal microorganisms on paper currencies.

In this respect, the paper currency sterilization system according to the present invention substantially departs from the conventional concepts and designs of the prior art, and in doing so provides an apparatus primarily developed for the purpose of killing all viral and fungal microorganisms on paper currencies.

Therefore, it can be appreciated that there exists a continuing need for a new and improved paper currency sterilization system which can be used for killing all viral and fungal microorganisms on paper currencies. In this regard, the present invention substantially fulfills this need.

SUMMARY OF THE INVENTION

In view of the foregoing disadvantages inherent in the known types of paper cleaning devices of known designs and configurations now present in the prior art, the present invention provides an improved paper currency sterilization system. As such, the general purpose of the present invention, which will be described subsequently in greater detail, is to provide a new and improved paper currency sterilization system and method which has all the advantages of the prior art and none of the disadvantages.

To attain this, the present invention essentially comprises a sterilization chamber. The sterilization chamber is in a generally rectilinear configuration. The sterilization chamber has a horizontal bottom wall and a parallel top wall. The sterilization chamber also has a vertical front wall, a parallel back wall and two side vertical parallel side walls there between. The front wall is formed with an input slot. The input slot is adjacent to the bottom wall. The back wall is formed with an output slot adjacent to the bottom wall. A conveyor system is provided. The conveyor system is comprised of two co-acting belts. The belts are fabricated of a Kevlar mesh. The Kevlar mesh has strands with enlarged apertures there through. The belts include a lower belt and an upper belt in facing contact throughout the entirety of their extents through the interior of the sterilization chamber. The belts form a reception area exterior of the sterilization chamber adjacent to the input end. The lower belt extends outwardly from the sterilization chamber a greater distance than the lower belt. In this manner a surface for receiving paper currency to be sterilized is provided. Provided next is a plurality of small diameter reversing rollers. The rollers include an input set of reversing rollers. The rollers are disposed one above the other in a vertical alignment interior of the sterilization chamber adjacent to the front wall. Also included is an output set of reversing rollers. This set of rollers is in vertical alignment interior of the sterilization chamber adjacent to the rear wall. The reversing rollers are adapted to convey the belts in contact with each other and with paper currency there between through the sterilization chamber from the input slot to the output slot for the movement of belts and paper currency in a serpentine path of travel. A pair of elastomeric input pressure rollers is also provided. The pressure rollers are provided interior of the sterilization chamber adjacent to the input slot. A pair of elastomeric output pressure rollers are provided within the sterilization chamber adjacent to the output slot. The pressure rollers are adapted to place pressure on the belts moving there between. The pressure rollers are fuller adapted to assist in the precluding the loss of high pressure from within the sterilization chamber. Provided next is a pair of elastomeric input pressure blocks. The pair of pressure blocks includes an upper block and a lower block interior of the sterilization chamber between the input slot. A pair of elastomeric output pressure blocks include an upper block and a lower block interior of the sterilization chamber between the output slot and the output pressure rollers. Coil springs bias the upper blocks toward the lower blocks. The pressure blocks and rollers are adapted to place pressure on the belts and paper currency moving there between. The pressure blocks and rollers are also adapted to assist in the precluding the loss of high pressure from within the sterilization chamber. A drying zone is provided next. The drying zone is provided within the sterilization chamber. Spring urged fingers are coupled to the blocks for holding the rollers in place during operation and use. The drying zone includes a vertical plate. The vertical plate is laterally spaced from the back wall with a slot adjacent to the upper wall and with a fan to dry and cool the belts and paper currency passing there through. Also provided is a heating element. The heating element is provided within the sterilization chamber. The heating element is adapted to increase the temperature within the sterilization chamber to about 270 degrees Fahrenheit. A pressure assembly is provided next. The pressure assembly is provided within the sterilization chamber. The pressure assembly is adapted to increase the pressure within the sterilization chamber to about two atmospheres. Provided last are drive members including a motor. The drive members are adapted to drive the belt at a speed at about 1 to 8 inches per second. The belts move in a serpentine fashion along a path of about 10 feet. In this manner each piece of paper currency is sterilized within the sterilization chamber with a high pressure and temperature for about ten minutes. The drive members also including upper guide rollers. The upper guide rollers move the upper belt in a return path of travel above the chamber. The drive members also include lower guide rollers. The lower guide rollers move the lower belt in a return path of travel below the chamber.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved paper currency sterilization system which has all of the advantages of the prior art paper cleaning devices of known designs and configurations and none of the disadvantages.

It is another object of the present invention to provide a new and improved paper currency sterilization system which may be easily and efficiently manufactured and marketed.

It is further an object of the present invention to provide a new and improved paper currency sterilization system which is of durable and reliable constructions.

An even further object of the present invention is to provide a new and improved paper currency sterilization system which is susceptible of a low cost of manufacture with regard to both materials and labor, and which accordingly is then susceptible of low prices of sale to the consuming public, thereby making such paper currency sterilization system economically available to the buying public.

Even still another object of the present invention is to provide a paper currency sterilization system for killing all viral and fungal microorganisms on paper currencies.

Lastly, it is an object of the present invention to provide a new and improved paper sterilization system comprises a chamber having one wall with an input slot and another wall with an output slot. A conveyor system is comprised of two co-acting belts, and upper and a lower. The belts are in facing contact. A plurality of rollers is provided. The rollers are adapted to convey the belts in contact with each other and with paper through the chamber from the input slot to the output slot. Also provided is a heating element. The heating element is adapted to increase the temperature to between about 150F and 400F degrees centigrade. A pressure assembly is provided. The pressure assembly is adapted to increase the pressure to between about 1ATM and 2ATM atmospheres. Drive members are provided. The drive members are adapted to drive the belt and paper at a speed sufficient to kill viral and fungal organisms on paper moving through the chamber.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is a cross-sectional view taken along line 4—4 of FIG. 2.

FIG. 5 is a cross-sectional view taken along line 5—5 of FIG. 4.

FIG. 6 is a cross-sectional view taken along line 6—6 of FIG. 5.

FIG. 7 is an end elevational view taken along line 7—7 of FIG. 1.

FIG. 8 is an end elevational view taken along line 8—8 of FIG. 7.

The same reference numerals refer to the same parts throughout the various Figures.

DESCRIPTION OF THE PREFERRED EMBODIMENT

Figure 1:
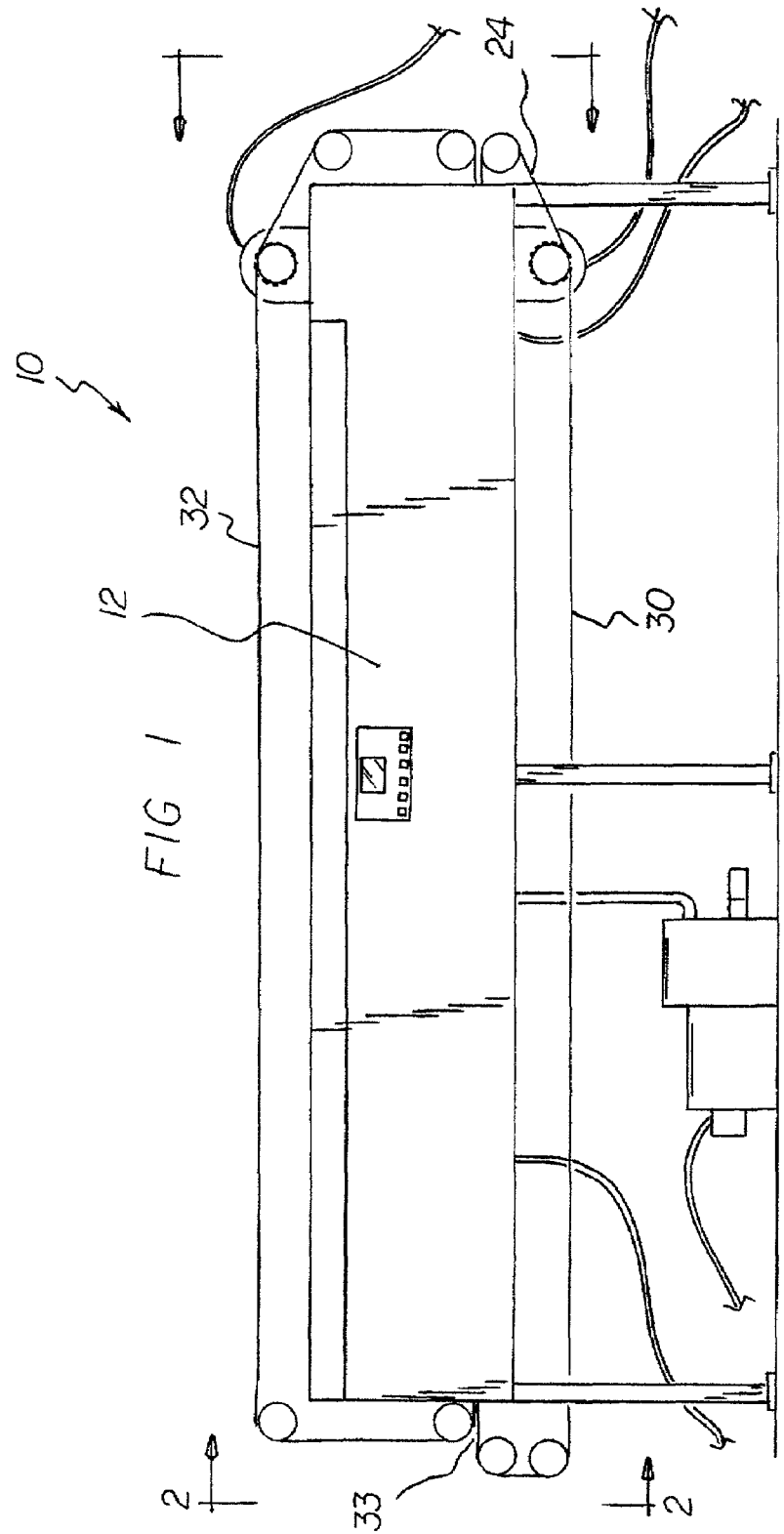
FIG. 1 is a side elevational view of the currency sterilization system constructed in accordance with the principles of the present invention.
Figure 2:
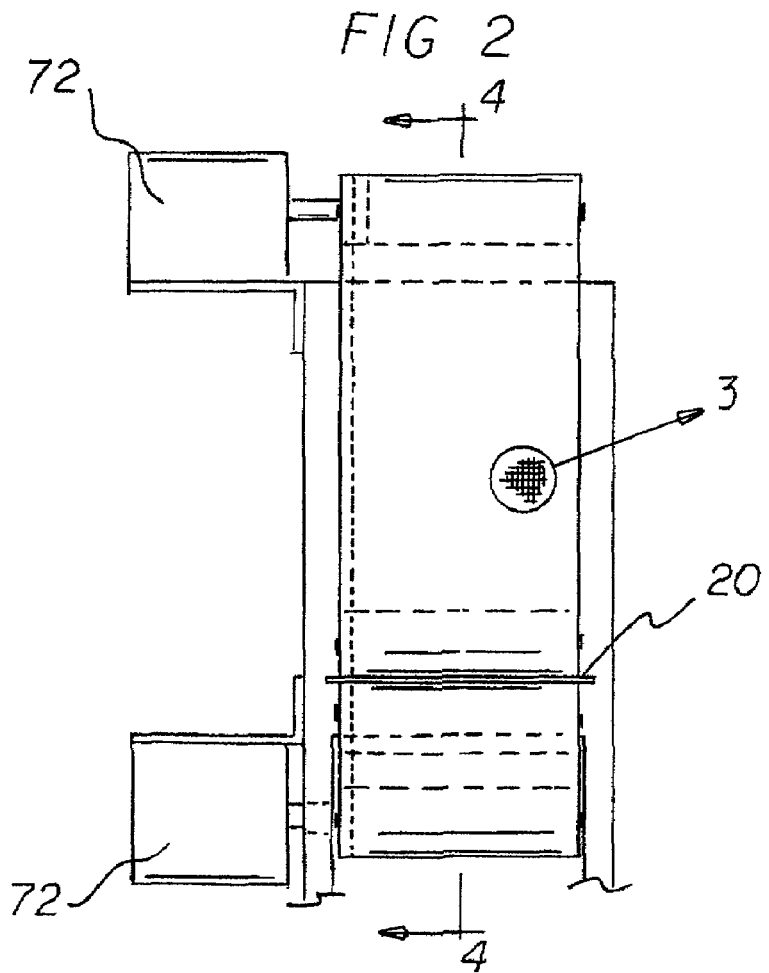
FIG. 2 is an end elevational view taken along line 2—2 of FIG. 1.
Figure 3:
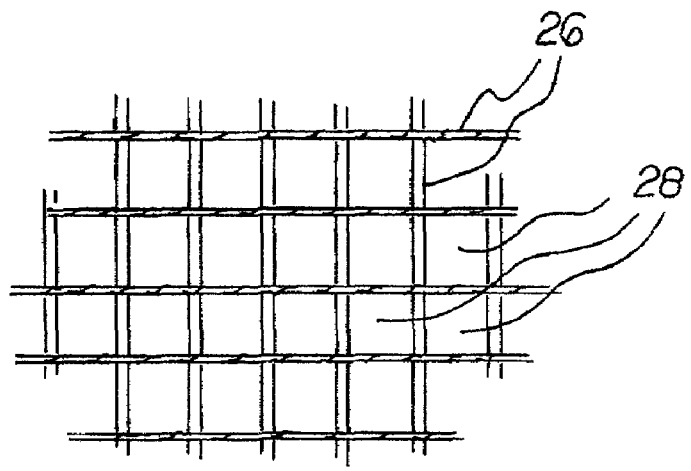
FIG. 3 is an enlarged perspective view of the belt taken at circle 3 of FIG. 2.

With reference now to the drawings, and in particular to FIG. 1 thereof, the preferred embodiment of the new and improved paper currency sterilization system embodying the principles and concepts of the present invention and generally designated by the reference numeral 10 will be described.

The present invention, the paper currency sterilization system 10 is comprised of a plurality of components. Such components in their broadest context include a chamber, a conveyor system, a plurality of rollers, a heating element, a pressure assembly, and drive members. Such components are individually configured and correlated with respect to each other so as to attain the desired objective.

First provided is a sterilization chamber 12. The sterilization chamber is in a generally rectilinear configuration. The sterilization chamber has a horizontal bottom wall 14 and a parallel top wall 16. The sterilization chamber also has a vertical front wall 17, a parallel back wall 18 and two side vertical parallel side walls 19 there between. The front wall is formed with an input slot 20. The input slot is adjacent to the bottom wall. The back wall is formed with an output slot 22 adjacent to the bottom wall.

A conveyor system 24 is provided. The conveyor system is comprised of two co-acting belts. The belts are fabricated of a Kevlar® (aramid synthetic fiber) mesh. The Kevlar mesh has strands 26 with enlarged apertures 28 there through. The belts include a lower belt 30 and an upper belt 32 in facing contact throughout the entirety of their extents through the interior of the sterilization chamber. The belts form a reception area exterior of the sterilization chamber adjacent to the input end. The lower belt extends outwardly from the sterilization chamber a greater distance than the lower belt. In this manner a surface 33 for receiving paper currency to be sterilized is provided.

Provided next is a plurality of small diameter reversing rollers 34. The rollers include an input set of reversing rollers 36. The rollers are disposed one above the other in a vertical alignment interior of the sterilization chamber adjacent to the front wall. Also included is an output set of reversing rollers 38. This set of rollers is in vertical alignment interior of the sterilization chamber adjacent to the rear wall. The reversing rollers are adapted to convey the belts in contact with each other and with paper currency there between through the sterilization chamber from the input slot to the output slot for the movement of belts and paper currency in a serpentine path of travel.

A pair of elastomeric input pressure rollers 42, 44 is also provided. The pressure rollers are provided interior of the sterilization chamber adjacent to the input slot. A pair of elastomeric output pressure rollers 46, 48 are provided within the sterilization chamber adjacent to the output slot. The pressure rollers are adapted to place pressure on the belts moving there between. The pressure rollers are fuller adapted to assist in the precluding the loss of high pressure from within the sterilization chamber.

Provided next is a pair of elastomeric input pressure blocks 50, 52. The pair of pressure blocks includes an upper block and a lower block interior of the sterilization chamber between the input slot. A pair of elastomeric output pressure blocks 54, 56 include an upper block and a lower block interior of the sterilization chamber between the output slot and the output pressure rollers. Coil springs 57 bias the upper blocks towards the lower blocks. The pressure blocks and rollers are adapted to place pressure on the belts and paper currency moving there between. The pressure blocks and rollers are also adapted to assist in the precluding the loss of high pressure from within the sterilization chamber. Spring urged fingers 58 are coupled to the blocks for holding the rollers in place during operation and use.

A drying zone 60 is provided next. The drying zone is provided within the sterilization chamber. The drying zone includes a vertical plate 62. The vertical plate is laterally spaced from the back wall with a slot 64 adjacent to the upper wall and with a fan 66 to dry and cool the belts and paper currency passing there through.

Also provided is a heating element 68. The heating element is provided within the sterilization chamber. The heating element is adapted to increase the temperature within the sterilization chamber to between 150 and 400 degrees Fahrenheit about 270 degrees Fahrenheit.

A pressure assembly 70 is provided next. The pressure assembly is provided within the sterilization chamber. The pressure assembly is adapted to increase the pressure within the sterilization chamber to between 1 and 4 atmospheres, preferably about two atmospheres.

Provided last are drive members including a motor 72. The drive members are adapted to drive the belt at a speed at between 1 and 8 inches per second, preferably about 3 inches per second. The belts move in a serpentine fashion along a path of about 10 feet. In this manner each piece of paper currency is sterilized within the sterilization chamber with a high pressure and temperature for about ten minutes. The drive members also including upper guide rollers 74. The upper guide rollers move the upper belt in a return path of travel above the chamber. The drive members also include lower guide rollers 76. The lower guide rollers move the lower belt in a return path of travel below the chamber.

The system is preferably programmable to either offer total sterilization and all that implies, or selective kill, that is if the fed only wants to kill anthrax and is not concerned over whatever else is on the bill the machine can be speed up and just kill anthrax or small pox, etc.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A paper currency sterilization system for killing all viral and fungal microorganisms on paper currencies comprising, in combination:

a sterilization chamber in a generally rectilinear configuration having a horizontal bottom wall and a parallel top wall, and with a vertical front wall and a parallel back wall and two side vertical parallel side walls there between, the front wall being formed with an input slot adjacent to the bottom wall and the back wall being formed with an output slot adjacent to the bottom wall;

a conveyor system comprised of two co-acting belts fabricated of aramid synthetic fiber mesh having strands with enlarged apertures there through, the belts including a lower belt and an upper belt in facing contact throughout the entirety of their extents through the interior of the sterilization chamber, the belts forming a reception area exterior of the sterilization chamber adjacent to the input end with the lower belt extending outwardly from the sterilization chamber a greater distance than the lower belt to provide a surface for receiving paper currency to be sterilized;

a plurality of small diameter reversing rollers including an input set of reversing rollers disposed one above the other in a vertical alignment interior of the sterilization chamber adjacent to the front wall and an output set of reversing rollers in vertical alignment interior of the sterilization chamber adjacent to the rear wall, the reversing rollers adapted to convey the belts in contact with each other and with paper currency there between through the sterilization chamber from the input slot to the output slot for the movement of belts and paper currency in a serpentine path of travel;

a pair of elastomeric input pressure rollers interior of the sterilization chamber adjacent to the input slot and a pair of elastomeric output pressure rollers within the sterilization chamber adjacent to the output slot, the pressure rollers adapted to place pressure on the belts moving there between and to assist in the precluding the loss of high pressure from within the sterilization chamber;

a pair of elastomeric input pressure blocks including an upper block and a lower block interior of the sterilization chamber between the input slot and the input pressure rollers, and a pair of elastomeric output pressure blocks including an upper block and a lower block interior of the sterilization chamber between the output slot and the output pressure rollers, the pressure rollers and blocks adapted to place pressure on the belts and paper currency moving there between and to assist in the precluding the loss of high pressure from within the sterilization chamber;

a drying zone within the sterilization chamber including a vertical plate laterally spaced from the back wall with a slot adjacent to the upper wall and with a fan to dry and cool the belts and paper currency passing there through;

a heating element within the sterilization chamber adapted to increase the temperature within the sterilization chamber to about 270 degrees Fahrenheit;

a pressure assembly within the sterilization chamber adapted to increase the pressure within the sterilization chamber to about two atmospheres; and drive members adapted to drive the belt at a speed at about 3 inches per second with the belts moving in a serpentine fashion along a path of about 10 feet whereby each piece of paper currency being sterilized is within the sterilization chamber with a high pressure and temperature for about ten minutes, the drive members also including upper guide rollers to move the upper belt in a return path of travel above the chamber and lower guide rollers to move the lower belt in a return path of travel below the chamber.

2. A paper sterilization system comprising:

a chamber in generally rectilinear configuration having a horizontal bottom wall and a parallel top wall, and with a vertical front wall and a parallel back wall and two side vertical parallel side walls there between, the front wall being formed with an input slot and the back wall being formed with an output slot;

a conveyor system comprised of two co-acting belts including a lower belt and an upper belt in facing contact throughout the entirety of their extents through the interior of the chamber;

a plurality of rollers adapted to convey the belts in contact with each other and with paper there between through the chamber from the input slot to the output slot;

a heating element adapted to increase the temperature within the chamber to between about 150 and 400 degrees Fahrenheit;

a pressure assembly adapted to increase the pressure within the chamber to between about 1 and 4 atmospheres;

drive members adapted to drive the belt and paper at a speed sufficient to kill all viral and fungal organisms on paper moving through the chamber while the heat element is producing a temperature between about 150 and 400 degrees Fahrenheit and while the pressure assembly produces pressures between 1 and 4 atmospheres; and a pair of input rollers interior of the chamber adjacent to the input slot and a pair of output rollers within the chamber adjacent to the output slot, the pressure rollers adapted place pressure on the belts and paper moving there between and to assist in precluding the loss of high pressure within the chamber.

3. The system as set forth in claim 2 and further including a pair of elastomeric input pressure blocks including an upper block and a lower block interior of the chamber adjacent to the input slot and a pair of elastomeric output pressure blocks including an upper block and a lower block interior of the chamber adjacent to the output slot, the pressure blocks adapted to place pressure on the belts and paper moving there between and to assist in the precluding the loss of high pressure from within the chamber.

4. The system as set forth in claim 2 wherein the input slot is adjacent to the bottom wall and the output slot is adjacent to the bottom wall.

5. The system as set forth in claim 2 wherein the pair of input rollers are elastomeric pressure rollers and the pair of output rollers are elastomeric pressure rollers.

* * * * *